United States Patent [19]
Brown et al.

[11] Patent Number: 5,220,841

[45] Date of Patent: Jun. 22, 1993

[54] ELECTROMAGNETIC FLUID FLOW TRANSDUCER

[75] Inventors: Samuel D. Brown, East Bend; Charles A. Barefoot; Charles R. Jones, both of Winston-Salem; Larry S. Stanley, Tobaccoville, all of N.C.

[73] Assignee: Carolina Medical Electronics, Inc., King, N.C.

[21] Appl. No.: 626,514

[22] Filed: Dec. 12, 1990

[51] Int. Cl.$^5$ .............................................. G01L 3/18
[52] U.S. Cl. ........................... 73/861.12; 73/861.13; 128/691
[58] Field of Search ........... 73/861.11, 861.12, 861.13; 128/691

[56] References Cited

U.S. PATENT DOCUMENTS

| | | | |
|---|---|---|---|
| 4,195,515 | 4/1980 | Smoll | 73/861.13 |
| 4,346,604 | 8/1982 | Snook et al. | 73/861.12 |
| 4,881,413 | 11/1989 | Georgi et al. | 73/861.12 |

OTHER PUBLICATIONS

Kolin, Alexander. "Electromagnetic Blood Flow Meters"; Oct. 23, 1959. Science: vol. 130. pp. 1088–1097.

Primary Examiner—Herbert Goldstein
Assistant Examiner—Elizabeth L. Shopbell

[57] ABSTRACT

An electromagnetic fluid flow transducer formed from an electromagnetic assembly having two electromagnet units and a tubular flow contact assembly to measure fluid flow velocity and fluid volume in ionic solutions. Each electromagnet unit includes a core and a winding on the core, and a housing maintains the electromagnet units and their cores and windings in a predetermined relationship with each other. A plurality of electrode receptacles are formed in the housing proximate the flux field created by the electromagnetic assembly. The tubular flow contact assembly includes a tubular member, and four conductive electrodes positioned in and extending from the internal surface of the tubular member where fluid flow occurs. The electrode receptacles in the housing cooperatively receive the conductive electrodes in the tubular member when the tubular flow contact assembly is positioned between the electromagnet units to obtain fluid flow and fluid velocity readings and display this information on appropriate fluid flow metering equipment.

28 Claims, 3 Drawing Sheets

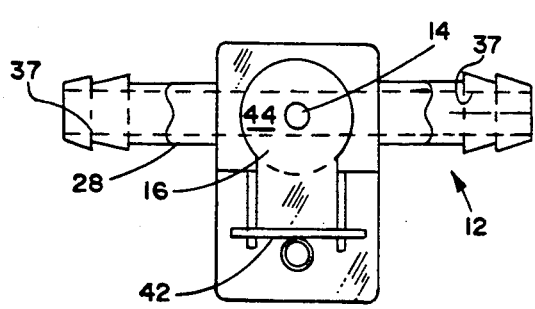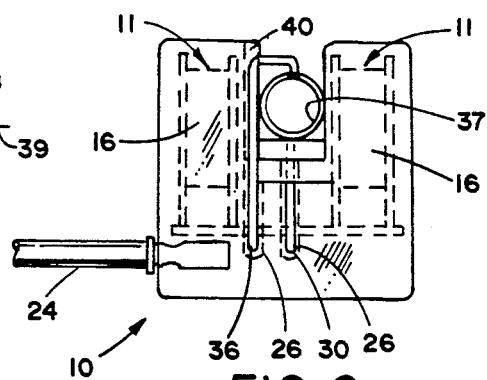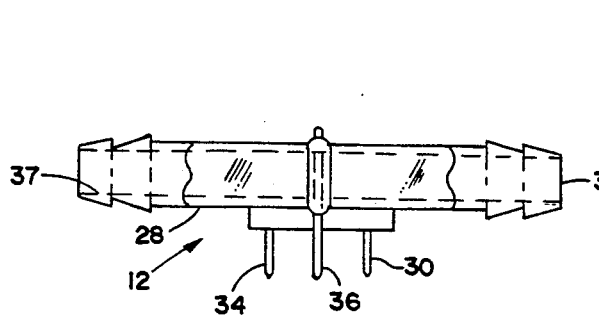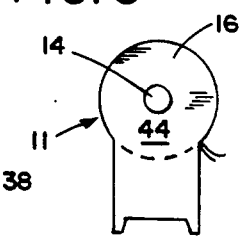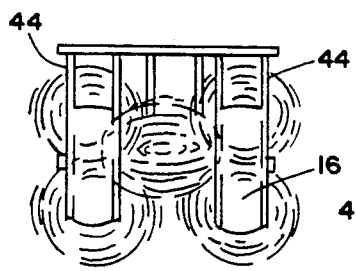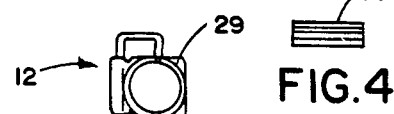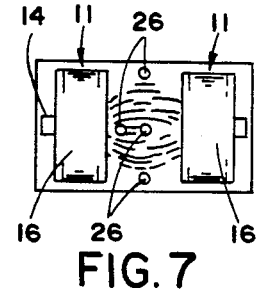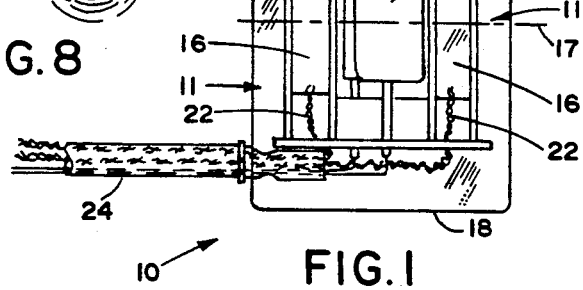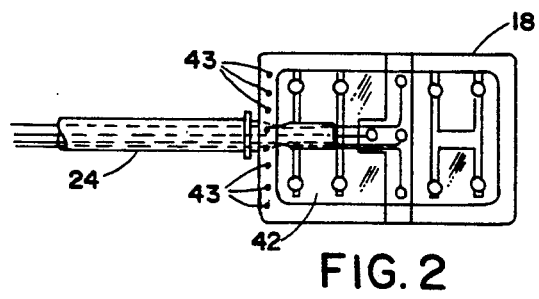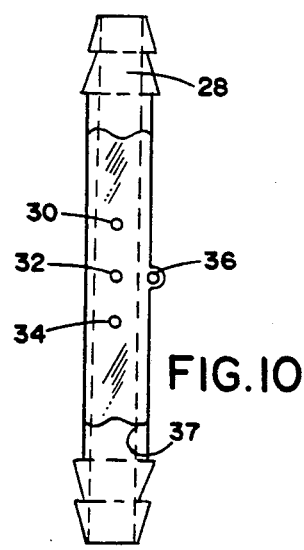

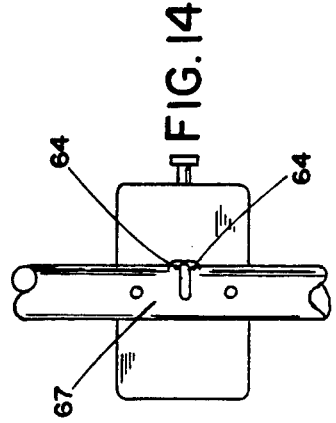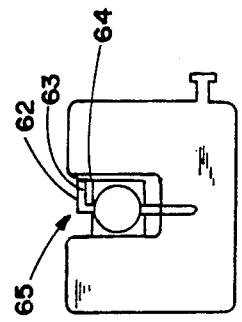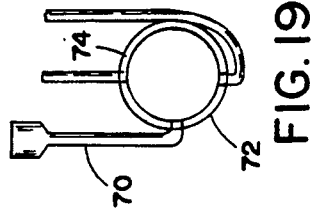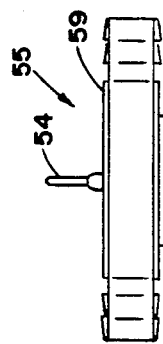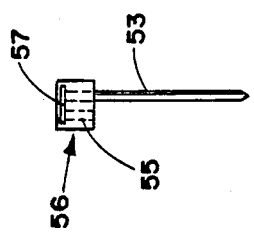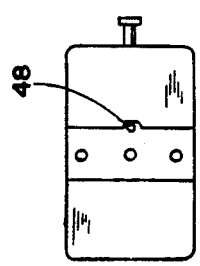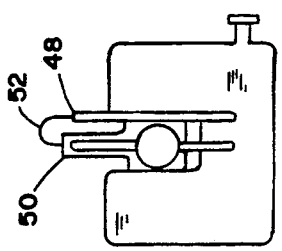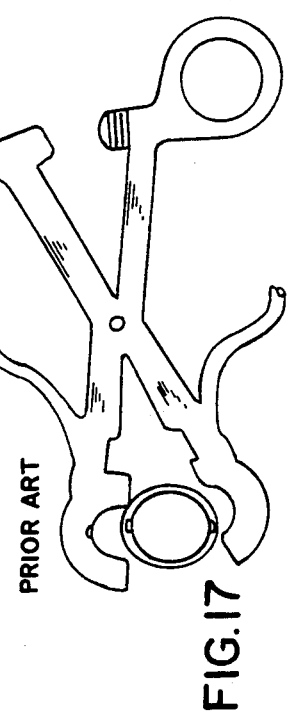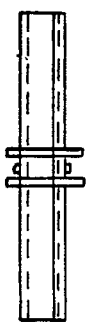

ELECTROMAGNETIC FLUID FLOW TRANSDUCER

BACKGROUND OF THE INVENTION

1. Field of the Invention

This invention relates to electromagnetic fluid flow transducers and more specifically to extracorporeal blood flow equipment for clinical use.

2. Description of the Prior Art

Electromagnetic fluid flow systems and more particularly blood flow transducers, have been used for many years and are typically described in structure and concept in U.S. Pat. Nos. 3,487,826; 3,516,399; and 3,805,768, the contents of which are incorporated herein by reference. The principle involved in these is references is Faraday's Law, i.e., passing a fluid, for example blood, either in a tube or blood vessel, at right angles to a magnetic field to produce an electromagnetic force in a direction perpendicular to the flux lines of the magnetic field and the direction of blood flow. The blood functions as a moving conductor cutting through the magnetic field. The electromotive force (voltage) is directly proportional to the velocity of flow and volume rate of flow, the strength of the magnetic field, and the length of the conductor. Such force can be measured by diametrically opposed electrodes positioned with respect to each other to form a line perpendicular to the lines of flux established by the magnetic field.

Heretofore the components of an extracorporeal electromagnetic flow transducer had to be maintained in a substantially rigid relationship each with the other to make certain that the device remained calibrated and functioned accurately. When all of the components were joined in such an arrangement, the device's stability was certain but the cannula of the unit was difficult to clean effectively and subject to abuse and damage from routine use and harsh cleaning procedures. Moreover, transducers of varying size had to be made to accommodate vessels and tubing of varying diameters.

Subsequently, it was found advantageous to provide a removable tubular flow contact assembly that could be easily cleaned or easily replaced, especially on clinical blood pump systems. Examples of such devices are the forceps probe illustrated herein and the embodiments disclosed in U.S. Pat. No. 4,195,515.

SUMMARY OF THE INVENTION

The improved fluid flow transducer made in accordance with the present invention is characterized by an electromagnetic assembly formed of a pair of matched electromagnet units and a tubular flow contact assembly which are releasably connectable to each other. This flow transducer is particularly useful in making flow measurements in an extracorporeal circuit. The electromagnet units each have a core and a winding on the core, and a housing maintains the electromagnet units and their cores and windings in a predetermined relationship with each other. A pair of conductors is associated with each winding extending from the winding to a power source. A plurality of electrode receptacles formed in the housing are positioned proximate the flux field created by the electromagnet units when the windings are energized. The tubular flow contact assembly is formed from a tubular member and four conductive electrodes connected in a predetermined relationship which from the interior wall of the tubular member. These electrodes cooperatively received by the electrode receptacles between the electromagnet units proximate the created flux field. The electromagnet units and tubular flow contact assembly are easily connected and disconnected mechanically and electrically. The electromagnetic assembly can be used with tubular members of different sizes and configurations by varying the inner diameter of the tubular member to match vessel diameters so that measurements can be made at different locations in an extracorporeal circuit by moving the electromagnetic assembly from one tubular flow contact assembly to another and using tubular members having appropriately sized inner diameters.

The tubular member of the tubular flow contact assembly is made preferably of a non-magnetic material connectable at each of its ends to an extracorporeal flow line carrying blood, plasma, saline or other ionic fluids such as those used to connect a heart/lung oxygenator, kidney dialysis machines and equipment used in critical drug monitoring or medicating procedures. In all such cases, the tubular member is inexpensive and therefore disposable thus avoiding risks to medical personnel operating cleaning equipment that has been used to treat victims of life-threatening diseases. Each electromagnet unit has a core and a winding on the core. The electromagnet units and their cores and windings are spaced from and opposite each other so that the flow contact assembly is received between the electromagnet units when the electrode receptacles mechanically and electrically receive the conductive electrodes. Conductors are connected to the windings and to the conductive electrodes and extend through a cable jacket to a conventional electromagnetic flow reading instrument having means to provide power to control, calibrate and process signals, and to display the readings induced in the electrodes of the transducer.

BRIEF DESCRIPTION OF THE DRAWINGS

FIG. 1 is a side elevational and disassembled view of the fluid flow transducer comprising the present invention with the housing removed but shown in hidden lines;

FIG. 2 is a plan view of the base carrying printed circuits and receptacles and a connected cable which is positioned in the housing (shown in hidden lines) of the present invention;

FIG. 3 is a side view of one of the magnet support bobbins carrying a core and encircling coil forming one of the electromagnet units of the present invention;

FIG. 4 is a plan view of one embodiment of the core shown in FIG. 3 and utilized in the present invention;

FIG. 5 is a front view of the flow transducer showing one of the electromagnet units and the tubular flow contact assembly with the electromagnet and flow contact assembly being mechanically and electrically connected;

FIG. 6 is a side elevational view of the transducer shown in FIG. 5;

FIG. 7 is a plan view of the electromagnetic assembly showing an important portion of the flux line configuration of the created magnetic field and the electrode receptacles;

FIG. 8 is a side elevational view of the electromagnetic assembly showing an important portion of the created magnetic field's flux line configuration;

FIG. 9 is a side elevational view of the tubular flow contact assembly utilized in the present invention;

FIG. 10 is a plan view of the tubular flow contact assembly of FIG. 9;

FIG. 11 is a side elevational sectional view of another embodiment of the fluid flow transducer comprising the present invention showing a conductor-connected electrode pin;

FIG. 12 is a side elevational sectional view of an alternative electrode configuration for the tubular flow contact assembly of FIG. 11 which may be utilized in the present invention;

FIG. 13 is a side elevational sectional view of another embodiment of the fluid flow transducer of the present invention;

FIG. 14 is a plan view of the embodiment of the transducer embodiment shown in FIG. 13;

FIG. 15 is a plan view of the housing of the electromagnetic assembly of the present invention;

FIG. 16 is a side elevational view of the embodiment of the tubular flow contact assembly utilized in the transducer shown in FIG. 11;

FIG. 17 is a plan view of a forceps style transducer utilizing a disposable cannula which represents prior art and an early effort to solve the problems now dealt with by the present invention;

FIG. 18 is a side elevational view of a tubular, releasable, connectable, and disposable cannula shown in FIG. 17;

FIG. 19 is an end view of a disposable cannula used in the present invention having a pressure port associated therewith utilizing a Becton-Dickinson Luer-Lok fitting;

DESCRIPTION OF THE PREFERRED EMBODIMENT

Figure 21:
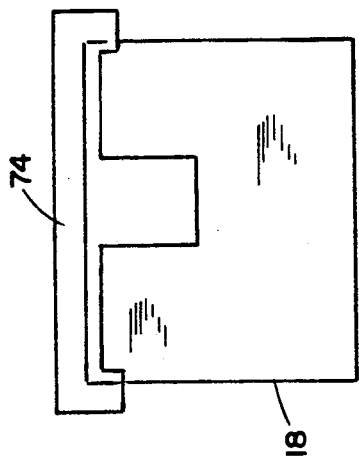
FIG. 21 is a side elevational view of the housing encompassing the electromagnetic assembly showing another alternative means of securing the tubular flow contact assembly within the electromagnetic assembly.
Figure 23:
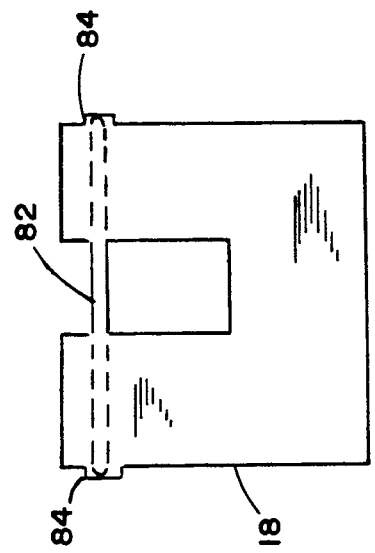
FIG. 23 is a side elevational view of the housing encompassing the electromagnetic assembly showing still another alternative means of securing the tubular flow contact assembly within the electromagnetic assembly.

Referring now to the drawings, the fluid flow transducer shown generally as 10 is comprised of two releasably securable parts, i.e., an electromagnetic assembly including a pair of matched electromagnet units shown generally as 11 and a tubular flow contact assembly shown generally as 12. The electromagnet units 11 each utilize a core 14 which supports a winding 16. The housing 18 (shown in hidden lines in FIG. 1), formed from a suitable plastic material such as Lexan, maintains the cores, windings and other elements subsequently to be described in a preselected relationship with each other so that an opening 20 is created in the housing between the electromagnet units 11 and their cores and windings 14, 16. In this configuration, the axes of the cores 14 and windings 16 are aligned along a common axis 17.

A pair of conductors 22 are associated with each winding 16 and extend therefrom through an output cable 24 and on to a power supply (not shown) which, upon activation, will energize windings 16 to create an electromagnetic field.

A plurality of electrode receptacles 26 (FIG. 7) are formed in housing 18 proximate magnetic field 27 created by electromagnet units 11 when windings 16 are energized. FIGS. 7 and 8 show the configuration of portions of the magnetic fields created when windings 16 are in the energized state.

The tubular flow contact assembly 12 (FIG. 9) includes a tubular member 28 and four conductive electrodes 30, 32, 34, 36 (FIG. 10) which are connected to and extend from the interior wall 37 of tubular member 28. Electrodes 30, 32, 34, 36 are mounted flush with interior wall 37 of tubular member 28 as shown in FIG. 5 and 9. Electrodes 32 and 36 are sensor electrodes positioned substantially diametrically opposed to each other flush with interior wall 37 of tubular member 28. Electrodes 30 and 34 are ground electrodes positioned on either side of, and preferably equidistant from, sensor electrodes 32, 34. Electrode 36 is J-shaped and partially encompasses exterior wall 29 of member 28 forming with electrode 32 a plane perpendicular to the plane formed by ground electrodes 30, 34.

Fluid or blood flow is through the bore 38 of tubular member 28 parallel to the axis 39 (FIG. 5) of tubular member 28 and perpendicular to the common axis 17 of cores 14 and windings 16. The sensor electrodes 32, 36 lie in a plane transverse to fluid flow, and the two ground electrodes lie in a plane parallel to fluid flow.

The configuration of cores 14 and windings 16 forming electromagnet units 11 results in a uniform flux field between the electromagnet units as shown in FIGS. 7 and 8 which is uniquely symmetrical and provides reliable flow readings when an appropriate flow metering instrument is connected to the transducer and activated.

A slight groove 40 is formed in housing 18 to partially receive electrode 36 and effectively serve as a guide to position the tubular flow contact assembly 12 precisely within the opening 20 between electromagnet units 11 of the electromagnetic assembly when the two members are urged together for mechanical and electrical connection. The windings 16 and cores 14 are supported on a base 42 (FIG. 2) which carries magnet support bobbins 44. Base 42 carries printed circuits and receptacles for conveniently securing and providing electrical and mechanical connections 43 for windings 16 and electrodes 30, 32, 34 and 36. Base 42 and its related components are encapsulated in housing 18 during the final assembly of the transducer. Electrodes 30, 32, 34, 36 are preferably formed of a non-corrosive conductive material, usually stainless steel, which efficiently contacts the fluid being measured.

Several alternative electrode configurations may be used in the tubular flow contact assembly comprising the present invention. These are illustrated in FIGS. 11, 12 and 13. Rather than use the J-shaped pin 36 as shown in FIG. 1, it has been found acceptable to use an essentially straight male pin 48 in conjunction with a separate female receptacle 50, the two elements being connected by a conductor 52. This configuration is less exacting in construction and easily utilized with the tubular flow contact assembly shown in FIG. 1. In this embodiment, the tubular flow contact assembly 55 (FIG. 16) effectively replaces the tubular flow contact assembly 12 of FIG. 9, and the conductor connected pins 48, 50 replace the J-shaped electrode 36.

Another alternative electrode receptacle combination embodiment is shown in FIG. 12 which is essentially a unitary member shown generally as 56 having a male portion 53 and a female portion 55a that can be directly connected to the tubular member 59 (FIG. 16) at electrode 54 when the tubular flow contact assembly is connected to the electromagnetic assembly (FIG. 11). The tubular flow contact assembly generally shown as 55 in FIG. 16 is easily capable of accommodating this alternative embodiment.

Yet another electrode embodiment is shown generally as 65 in FIGS. 13 and 14, the replacement for the J-shaped electrode 36 in FIG. 1 being an L-shaped pin 62, the horizontal portion 63 extending and nesting between two vertically upstanding pins 64. These pins connect with appropriate conductors on base 42. The tubular flow contact assembly 67, except for the differently configured electrode 62 described above, is essentially the same as that shown in FIGS. 1 and 9.

The use of two electromagnet units in the electromagnetic assembly of the present invention offers a number of advantages over conventionally used electromagnetic units. For example, positioning the winding about a straight core 14 is much easier to accomplish and does not require the use of sophisticated equipment or the time consuming hand wrapping that might otherwise be necessary. Moreover, the duplicate matched winding of the present invention result in a minimized use of iron for core material since the core is straight and short as opposed to a circular or substantially U-shaped core that might otherwise be utilized. The use of a pair of balanced windings 16 and cores 14 to form the electromagnet units comprising the electromagnetic assembly of the present invention results in a symmetrical flux field in contrast to an unbalanced flux field that might result from the use of other configured core and coil combinations.

The use of the two ground electrodes 30, 34 minimizes the effect of eddy currents and circulating ground currents in the system. It produces a balanced ground effect to improve monitoring stability and to ground out unwanted noise signals, particularly those attributable to common 50/60 cycle currents and harmonics thereof.

The present invention can be easily adapted to utilize a pressure port 70 shown in FIG. 19. Pressure port 70 is directly inserted into the wall 72 of cannula 74, and port 70 can be then directly connected to a pressure monitoring instrument, a number of which are commercially available.

From the foregoing, it can be seen that it is possible by utilizing the present invention to vary the size of the tubular member interior to accommodate vessels and tubing of differing sizes and yet still use the same electromagnetic structure. Different sizes of tubular members can be color coded to minimize the possibility of improper usage and to specifically designate precise sizes.

A ground ring may be added to the tubular member to replace the ground electrodes thus providing an alternative means to stabilize the electrical system and ensure accurate and consistent readings. To further ensure such consistent readings, shields may be used over the electrode and winding conductors to prevent any exterior or cross-conductor field interference.

Figure 20:
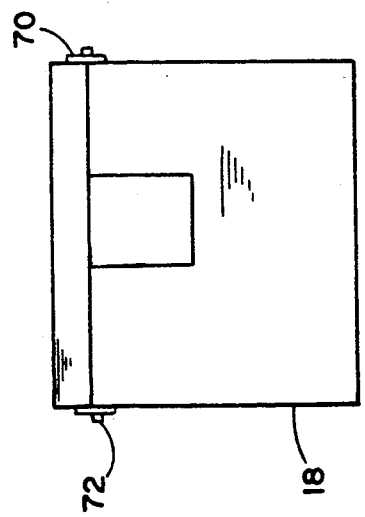
FIG. 20 is a side elevational view of the housing encompassing the electromagnetic assembly of the present invention showing an alternative means of securing the tubular flow contact assembly within the electromagnetic assembly.
Figure 22:
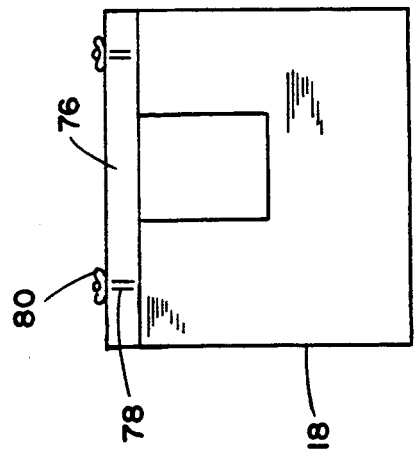
FIG. 22 is a side elevational view of the housing encompassing the electromagnetic assembly showing yet another alternative means of securing the tubular flow contact assembly within the electromagnetic assembly.

The housing 18 of the present invention can be treated to even more securely receive and hold in place the tubular flow contact means, and a variety of devices to incorporate this objective is shown in FIGS. 20, 21, 22 and 23. For example, a releasably securing member can be positioned to close the housing and encompass the tubular flow contact means between the electromagnetic units. One such closure member is shown in FIG. 20 as being held in place by a hinge 71 and hasp 73 combination. A frictional fit closure member 74 is shown in FIG. 21, and a closure member 76 is releasably secured by a screw 78 and wing nut 80 combination is shown in FIG. 22. A bar 82 comprises the closure member in FIG. 23 which preferably will be held securely in place by threadable receptors 84.

Thus an improved transducer for making extracorporeal blood flow measurements is formed from two releasably connectable sections, one section being formed from two electromagnet units and the other section being formed from a flow contact tubular member which will accommodate fluid flow and, through its supported electrodes, transmit meaningful fluid flow signals to be read by an associated signal-processing read-out device (not shown). The electromagnet assembly can be used interchangeably with a plurality of flow contact assemblies positioned at various extracorporeal locations. The flow contact assemblies are relatively inexpensive and can be recycled or discarded after use. The device will also allow various sizes of tubular flow contact assemblies to be used with the same electromagnetic assembly.

While there has been shown a preferred embodiment of a transducer for measuring the flow rate of conductive fluids, any number of modifications can be made in the electromagnetic assembly and the tubular flow contact assembly without departing from the spirit and purpose of the present inventive concept. Such modifications are contemplated and are deemed to be well within the scope of the appended claims.

What is claimed is:

1. A flow transducer for measuring quantitatively the flow of conductive fluids comprising: an electromagnetic assembly having two (2) circular electromagnet units each of which utilizes a core and a winding on said core; a pair of conductors associated with each winding; a housing encompassing said electromagnet units and sustaining said units in a predetermined side-by-side relationship sharing a common center line; four electrode receptacles positioned proximate the magnetic field created by said cores and windings when said windings are energized; and tubular flow contact means including a tubular member, four conductive electrodes connected to and extending from said tubular member all movable between said electromagnet units and back again, said electrode receptacles cooperatively receiving said conductive electrodes when said flow contact means is positioned between said electromagnet units.

2. The transducer as claimed in claim 1 wherein said housing has guide means for guiding said tubular flow contact means into proper electrical and mechanical engagement with said electromagnetic assembly, said guide means including a groove in said housing cooperatively receiving a conductive electrode extending in the direction of tubular flow contact means movement between the electromagnet units.

3. The transducer as claimed in claim 1 wherein said conductive electrodes include two sensor electrodes and two ground electrodes.

4. The transducer as claimed in claim 1 wherein the common center line of said windings is perpendicular to fluid flow.

5. The transducer as claimed in claim 3 wherein the two sensor electrodes are positioned between said two ground electrodes.

6. The transducer as claimed in claim 3 wherein the two sensor electrodes lie in a plane transverse to fluid flow.

7. The transducer as claimed in claim 3 wherein the two ground electrodes lie in a plane parallel to fluid flow.

8. The transducer as claimed in claim 2 wherein said conductive electrodes include two sensor electrodes and two ground electrodes.

9. The transducer as claimed in claim 3 wherein the common center line of said windings is perpendicular to fluid flow.

10. The transducer as claimed in claim 3 wherein the two sensor electrodes are positioned between said two ground electrodes.

11. The transducer as claimed in claim 10 wherein the two sensor electrodes lie in a plane transverse to fluid flow.

12. The transducer as claimed in claim 11 wherein the two ground electrodes lie in a plane parallel to fluid flow.

13. The transducer as claimed in claim 1 wherein said windings are spaced from and opposite each other to receive said flow contact means therebetween.

14. The transducer as claimed in claim 3 further comprising a base encompassed within said housing supporting said windings and cores.

15. The transducer as claimed in claim 12 further comprising a base encompassed within said housing and supporting said windings and cores.

16. The transducer as claimed in claim 14 further comprising a pressure port located in said tubular member.

17. The transducer as claimed in claim 14, said housing having guide means formed therein to guide and position said tubular flow contact means between said electromagnet units to achieve mechanical and electrical connection.

18. The transducer as claimed in claim 16, said housing having guide means formed therein to guide and position said tubular flow contact means between said electromagnet units to achieve mechanical and electrical connection.

19. The transducer as claimed in claim 1 wherein said tubular member is formed of a non-magnetic material.

20. The transducer as claimed in claim 18 wherein said tubular member is formed of a non-magnetic material.

21. The transducer as claimed in claim 8 wherein one of said sensor electrodes is J-shaped, partially encircles said tubular member, and is cooperatively received by said guide means groove.

22. The transducer as claimed in claim 20 wherein one of said sensor electrodes is J-shaped, partially encircles said tubular member, and is cooperatively received by said guide means groove.

23. The transducer as claimed in claim 18 wherein said tubular member is formed of a non-metallic material.

24. A transducer as claimed in claim 21 further comprising a closure member having releasably securing means to close said housing and encompassing said tubular flow contact means between said electromagnet units.

25. The transducer as claimed in claim 24 wherein said releasably securing means is a hinge and hasp combination.

26. The transducer as claimed in claim 24 wherein the releasably securing means is a screw and wing nut combination.

27. The transducer as claimed in claim 24 wherein said releasably securing means is a frictional fit with said housing.

28. The transducer as claimed in claim 24 wherein said releasably securing means is a bar extending through said housing.

* * * * *